United States Patent
Fischvogt et al.

(10) Patent No.: US 12,029,389 B2
(45) Date of Patent: Jul. 9, 2024

(54) TWO-POSITION ACTUATION WITH BACKLASH COMPENSATION FOR SURGICAL DEVICES

(71) Applicant: Covidien LP, Mansfield, MA (US)

(72) Inventors: Gregory W. Fischvogt, Reno, NV (US); Kevin S. Sniffin, Roxbury, CT (US); David A. Nicholas, Trumbull, CT (US)

(73) Assignee: COVIDIEN LP, Mansfield, MA (US)

( * ) Notice: Subject to any disclaimer, the term of this patent is extended or adjusted under 35 U.S.C. 154(b) by 767 days.

(21) Appl. No.: 17/153,457

(22) Filed: Jan. 20, 2021

(65) Prior Publication Data

US 2021/0298576 A1    Sep. 30, 2021

Related U.S. Application Data

(60) Provisional application No. 63/000,645, filed on Mar. 27, 2020.

(51) Int. Cl.
*A61B 1/00* (2006.01)
*A61B 1/313* (2006.01)
*A61B 17/00* (2006.01)

(52) U.S. Cl.
CPC ........ *A61B 1/00133* (2013.01); *A61B 1/3132* (2013.01); *A61B 17/00234* (2013.01); *A61B 2017/00296* (2013.01); *A61B 2017/00367* (2013.01)

(58) Field of Classification Search
CPC .......................... A61B 1/00133; A61B 1/3132
USPC ............................................................ 606/1
See application file for complete search history.

(56) References Cited

U.S. PATENT DOCUMENTS

| | | | |
|---|---|---|---|
| 3,459,187 A | 8/1969 | Pallotta | |
| 5,732,806 A * | 3/1998 | Foshee | A61B 17/068 |
| | | | 192/30 R |
| 2014/0005705 A1 | 1/2014 | Weir et al. | |

FOREIGN PATENT DOCUMENTS

WO        9736545 A1    10/1997

* cited by examiner

*Primary Examiner* — Nadia A Mahmood
(74) *Attorney, Agent, or Firm* — Carter, DeLuca & Farrell, LLP

(57) ABSTRACT

This disclosure relates to an articulation assembly configured for backlash compensation for use with surgical devices. The articulation assembly includes an articulation lever assembly configured to reduce axial backlash. The articulation assembly further includes an articulation joint configured to reduce lateral backlash.

18 Claims, 15 Drawing Sheets

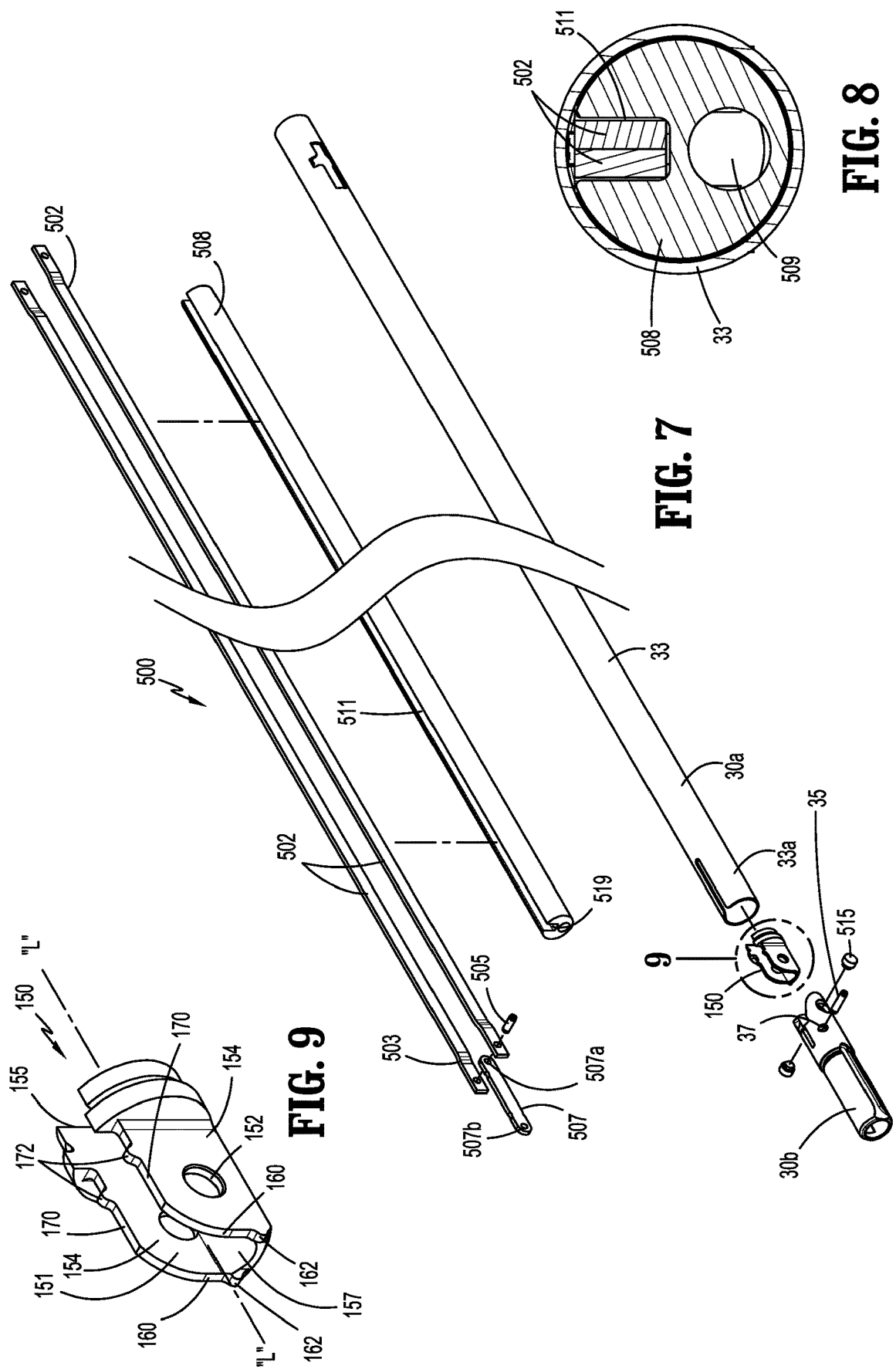

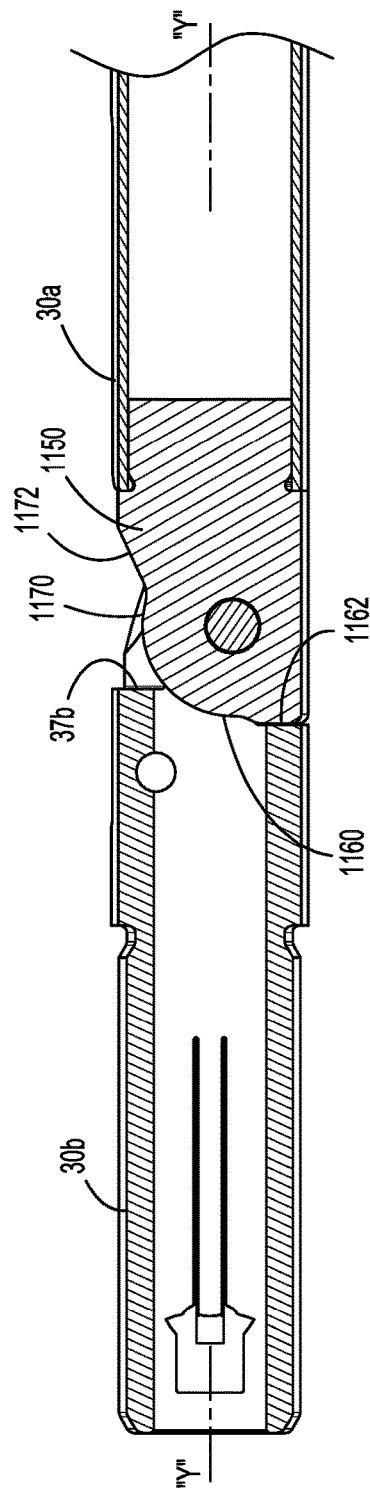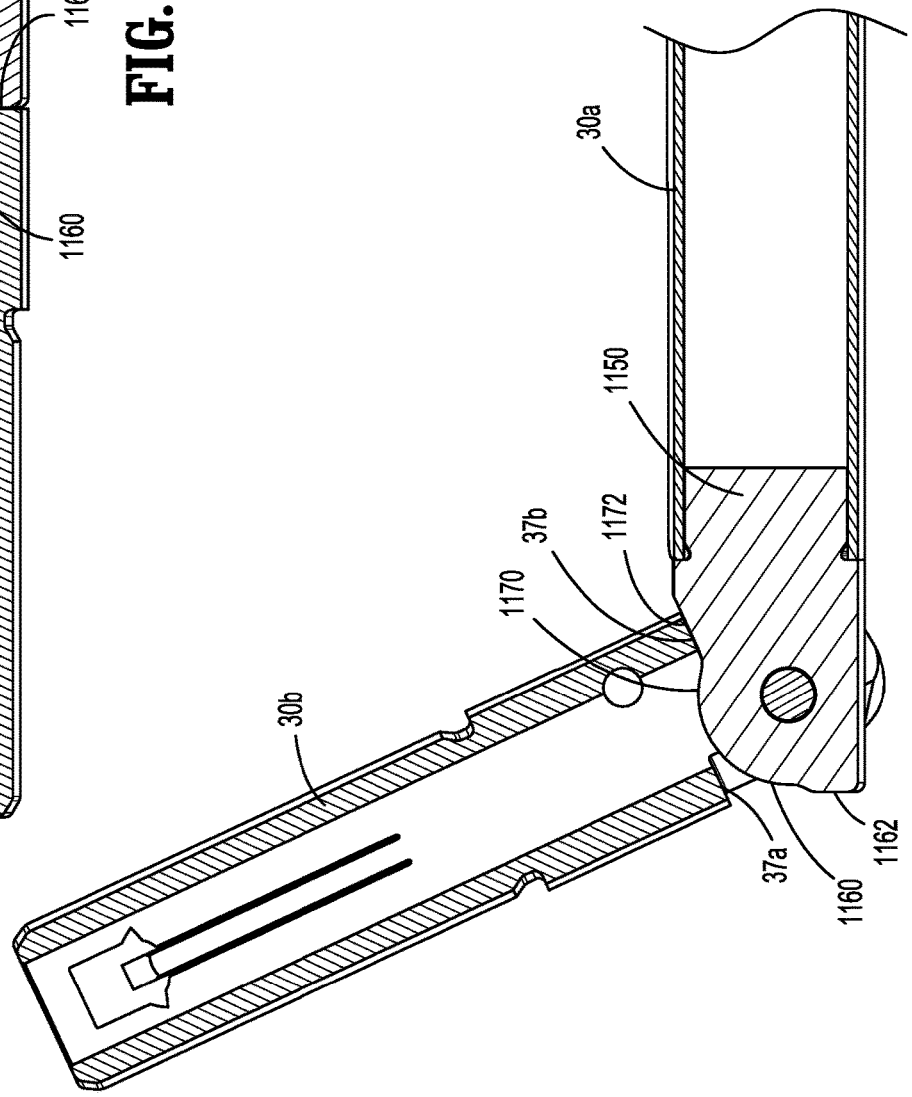

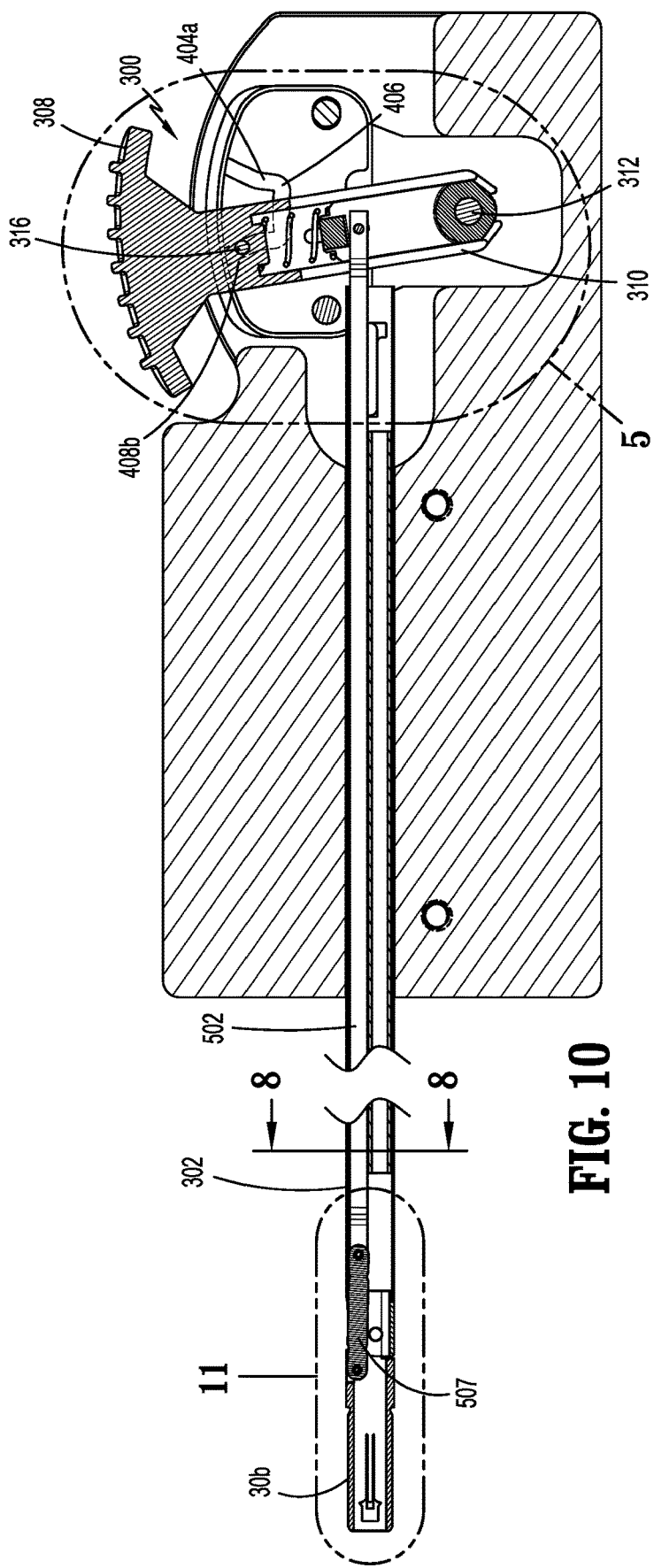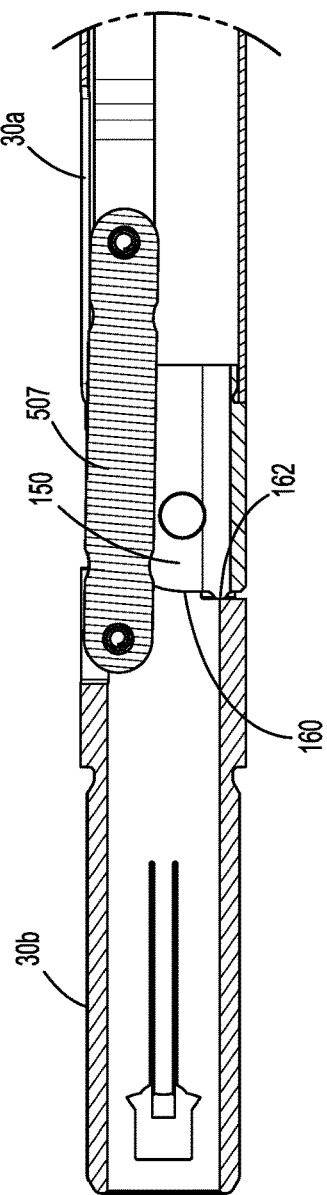

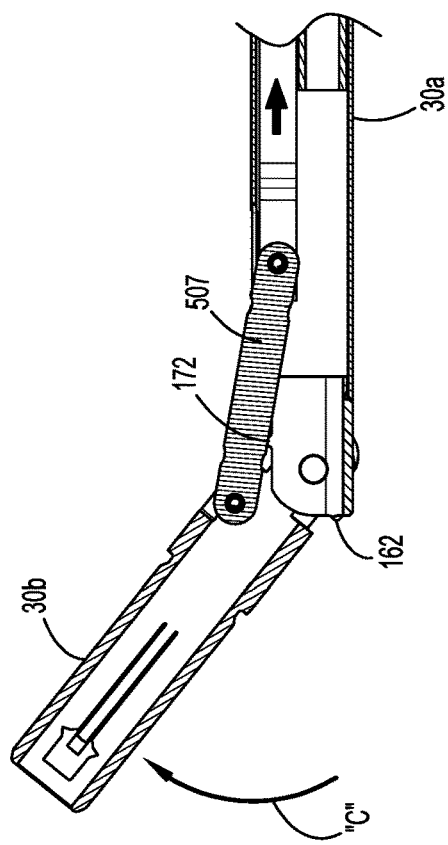
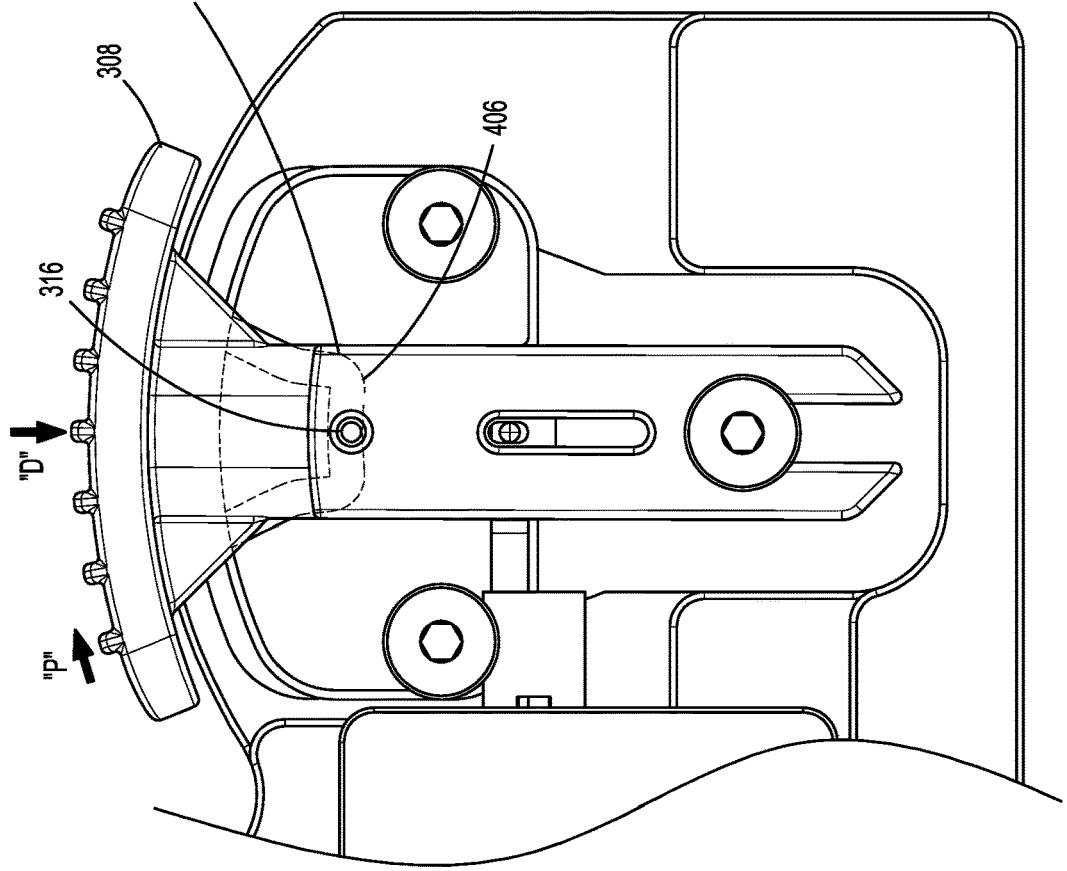
FIG. 13
FIG. 12

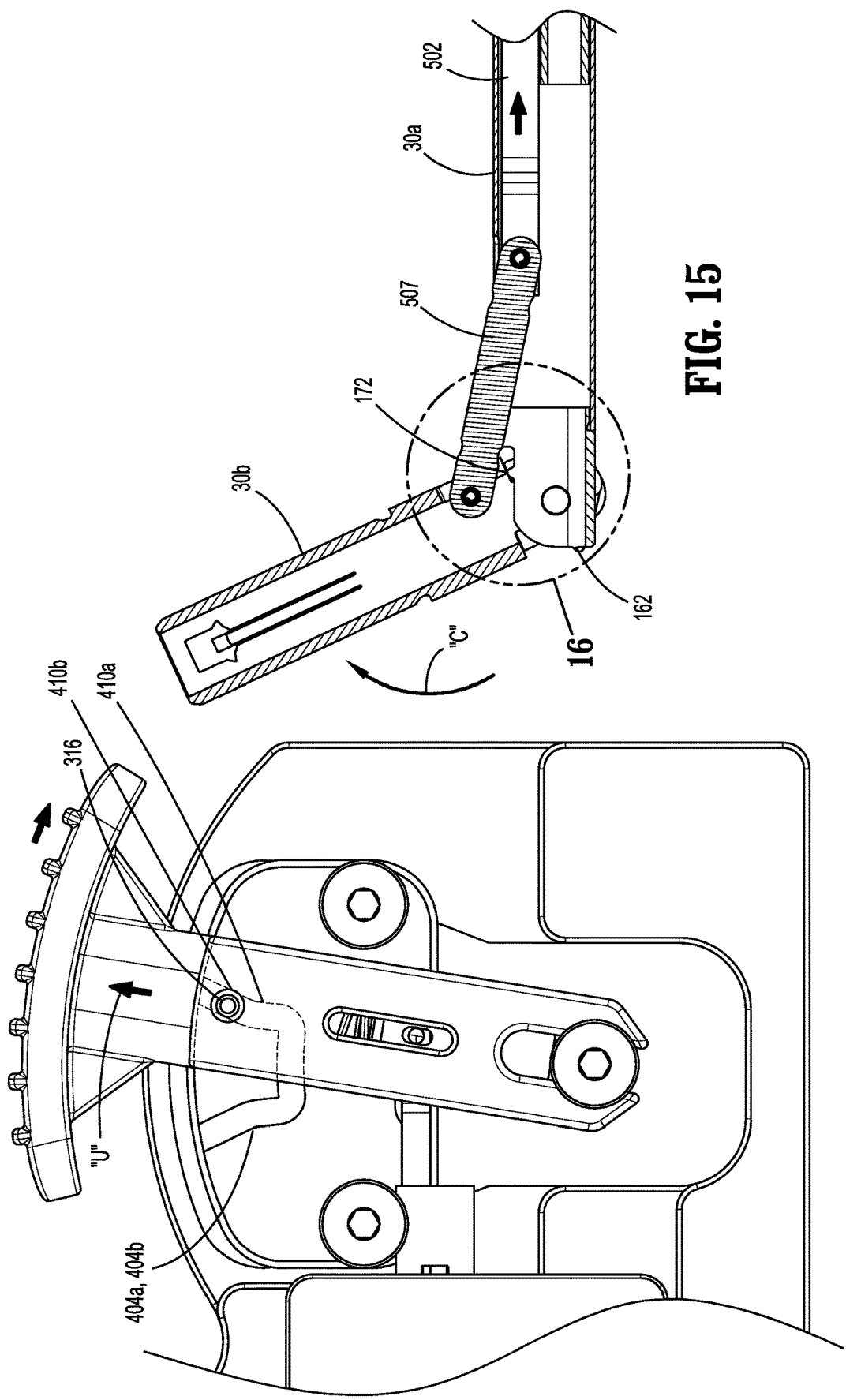

TWO-POSITION ACTUATION WITH BACKLASH COMPENSATION FOR SURGICAL DEVICES

CROSS-REFERENCE TO RELATED APPLICATIONS

This application claims the benefit of and priority to U.S. Provisional Patent Application Ser. No. 63/000,645, filed Mar. 27, 2020, the disclosure of which is incorporated by reference herein in its entirety.

TECHNICAL FIELD

This disclosure relates to surgical devices for performing endoscopic surgical procedures. More specifically, this disclosure relates to an articulation assembly configured for backlash compensation for use with the surgical devices.

BACKGROUND

During laparoscopic or endoscopic surgical procedures, access to a surgical site is achieved through a small incision or through a narrow cannula inserted through a small entrance wound in a patient. Because of limited area to access the surgical site, many endoscopic surgical devices include mechanisms for articulating the tool assembly of the device. Typically, the articulation mechanism is controlled by an actuator which has to be manipulated by a surgeon to properly orient the tool assembly in relation to tissue to be treated.

SUMMARY

In accordance with this disclosure, an articulation assembly for use with a surgical instrument includes a first portion, an articulation joint coupled to the first portion, a second portion pivotably coupled to the articulation joint, and an articulation assembly. The second portion is pivotably coupled to the articulation joint such that the second portion is transitionable between a surgical instrument straight configuration in which the second portion is axially aligned with the first portion, and a surgical instrument articulated configuration in which the second portion is axially offset from the first portion. The articulation assembly includes a body portion, an articulation lever assembly operatively coupled with the second portion, and a camming support. The articulation lever assembly includes a camming pin, a housing, a slider extending from the housing, and a lever. The housing defines a cavity and lateral bores configured to receive the camming pin therethrough such that the camming pin extends laterally outward from the housing. The lever is pivotably coupled to the body portion about a first pivot. The lever is at least partially received in the cavity of the housing. The camming support defines a camming groove configured to cammingly engage the camming pin. The camming groove includes a transition portion, a distal portion, and a proximal portion. The transition portion is interposed between the distal and proximal portions. The proximal and distal portions define respective angles with respect to the transition portion. The slider of the articulation lever assembly is transitionable between a distal position, in which, the camming pin is in the distal portion of the camming groove and the second portion is in the surgical instrument straight configuration, and a proximal position, in which, the camming pin is in the proximal portion of the camming groove and the second portion is in the surgical instrument articulated configuration.

In an aspect, the articulation assembly may include an articulation actuation assembly operatively coupling the lever of the articulation lever assembly with the second portion such that pivoting of the lever causes transition of the second portion between the surgical instrument straight and articulated configurations.

In another aspect, the articulation actuation assembly may include a translating rod and a linkage. The translating rod may be coupled to the lever of the articulation lever assembly such that pivoting of the lever imparts axial displacement to the translating rod. The linkage may pivotably couple the second portion and the translating rod.

In yet another aspect, the linkage of the articulation actuation assembly may be configured to be received in the articulation joint when the second part is in the surgical instrument straight configuration.

In still yet another aspect, the lever of the articulation lever assembly may include a biasing member configured to be received in the cavity of the housing such that the slider is biased away from the first pivot.

In still yet another aspect, the transition portion of the camming groove may be substantially parallel to a longitudinal axis defined by the body portion.

In an aspect, the housing of the articulation lever assembly may be interposed between two halves of the camming support.

In another aspect, the housing and the slider of the articulation lever assembly may be formed as a single construct.

In another aspect, the distal portion of the camming groove may include a first distal portion defining a first angle with respect to the transition portion, and a second distal portion defining a second angle with respect to the transition portion. The first distal portion may be interposed between the transition portion and the second distal portion. The first angle may be different from the second angle.

In yet another aspect, the second angle may be greater than the first angle.

In still yet another aspect, the proximal portion of the camming groove may include a first proximal portion defining a third angle with respect to the transition portion, and a second proximal portion defining a fourth angle with respect to the transition portion. The first proximal portion may be interposed between the transition portion and the second proximal portion. The third angle may be different from the fourth angle.

In still yet another aspect, the fourth angle may be greater than the third angle.

In an aspect, the first proximal portion may be substantially perpendicular to the transition portion.

In an aspect, the first distal portion may be substantially perpendicular to the transition portion.

In another aspect, the camming pin may be configured to rest in the second proximal and distal portions of the camming groove when the slider is in the respective proximal and distal positions.

In accordance with another aspect of this disclosure, an articulation system for use with a surgical instrument includes a first portion, an articulation joint coupled to the first portion, a second portion pivotably coupled to the articulation joint, and an articulation assembly. The articulation joint defines a cavity therebetween. The articulation joint includes a distal surface including a first stop, and an engagement surface including a second stop. The second portion is transitionable between a surgical instrument straight configuration, in which, the second portion is axially aligned with the first portion and engages the first stop of the articulation joint, and a surgical instrument articulated configuration, in which, the second portion is axially offset from the first portion and engages the second stop of the articulation joint. The articulation assembly includes a body portion, an articulation lever assembly operatively coupled with the second portion, and a camming support. The articulation lever assembly includes a housing defining a cavity therein, a camming pin extending laterally outward from the housing, a slider extending from the housing, and a lever pivotably coupled to the body portion and at least partially received in the cavity of the housing. The camming support defines a camming groove configured to cammingly engage the camming pin. The camming groove includes a transition portion, a distal portion, and a proximal portion. The transition portion is interposed between the distal and proximal portions. The proximal and distal portions define respective angles with respect to the transition portion. The slider of the articulation lever assembly is transitionable between a distal position, in which, the camming pin is in the distal portion of the camming groove such that the second portion is in the surgical instrument straight configuration, and a proximal position, in which, the camming pin is in the proximal portion of the camming groove such that the second portion is in the surgical instrument articulated configuration.

In an aspect, the second portion may include a first proximal surface configured to engage the first stop of the articulation joint when the second portion is in the surgical instrument straight configuration, and a second proximal surface configured to engage the second stop of the articulation joint when the second portion is in the surgical instrument articulated configuration.

In another aspect, the first or second stop of the articulation joint may be formed of deformable or resilient materials.

In yet another aspect, the articulation joint may include opposing lateral walls defining the cavity therebetween. The articulation joint may include opposing portions having a closed portion and an opening between the opposing lateral walls. The opposing lateral walls may include respective distal surfaces extending between the closed portion and the opening. The distal surfaces may include respective first stops. The opposing lateral walls may include respective engagement surfaces disposed adjacent the opening. The engagement surfaces may include respective second stops.

In an aspect, the first stops may be protrusions extending from the respective distal surfaces of the opposing lateral walls.

In another aspect, the second stops may be protrusions extending from the respective engagement surfaces of the opposing lateral walls.

In yet another aspect, the first stops may be planar surfaces substantially orthogonal to a longitudinal axis defined by the articulation joint.

In still yet another aspect, the second stops may be planar surfaces defining respective acute angles with a longitudinal axis defined by the articulation joint.

In still yet another aspect, each lateral wall may include an arcuate portion interconnecting the first and second stops.

In another aspect, the engagement surface may be substantially parallel to a longitudinal axis defined by the articulation joint.

In yet another aspect, the distal surfaces may define an arcuate profile or a curvature.

In still yet another aspect, the articulation assembly may further include an articulation actuation assembly operatively coupled with the lever such that pivoting of the lever between the proximal and distal positions causes axial displacement of the articulation actuation assembly.

In an aspect, the second portion may include opposing laterals wings defining a mouth dimensioned to receive the opposing lateral walls of the articulation joint therein. Each lateral wing may define a bore and each lateral wall may define a hole in registration with the bore.

In another aspect, the second portion may be pivotably coupled to the articulation joint by a pair of pins. Each pin may have a head portion, a neck portion, and a shoulder connecting the neck portion to the head portion. The neck portion may have a diameter smaller than a diameter of the head portion. The head portion may be fixedly received in the bore of the corresponding lateral wing and the neck portion may extend through the hole of the corresponding lateral wall such that the shoulder engages the corresponding lateral wall.

In yet another aspect, the shoulder of the pin may be beveled or rounded.

In still yet another aspect, the lever of the articulation lever assembly may include a base portion pivotably coupled to the body portion about a pivot and a stem portion extending from the base portion and slidably received in the cavity of the housing. The stem portion may support a biasing member thereabout. The biasing member may be secured with the housing and the base portion to bias the housing away from the pivot.

In accordance with yet another aspect of this disclosure, a surgical tack applier includes a handle assembly, an endoscopic anchor retaining and advancing assembly, and an articulation assembly. The endoscopic anchor retaining and advancing assembly extends from the handle assembly and is configured to store and selectively release or fire a plurality of anchors therefrom. The endoscopic anchor retaining and advancing assembly includes a proximal tube portion, a distal tube portion, and an articulation joint coupled to the proximal tube portion. The distal tube portion is pivotably coupled to the articulation joint. The articulation assembly includes a body portion disposed within the handle assembly, an articulation lever assembly operatively coupled with the distal tube portion, and a camming support. The articulation lever assembly includes a camming pin, a housing defining a cavity and lateral bores configured to receive the camming pin therethrough such that the camming pin extends laterally outward from the housing, a slider extending from the housing, and a lever pivotably coupled to the body portion about a first pivot. The lever is at least partially received in the cavity of the housing. The camming support defines a camming groove configured to cammingly engage the camming pin. The camming groove includes a transition portion, a distal portion, and a proximal portion. The transition portion interposed between the distal and proximal portions. The proximal and distal portions define respective angles with respect to the transition portion. The slider of the articulation lever assembly is transitionable between a distal position, in which, the camming pin is in the distal portion of the camming groove such that the distal tube portion is axially aligned with the first portion, and a proximal position, in which, the camming pin is in the proximal portion of the camming groove such that the distal tube portion is axially offset from the proximal tube portion.

In an aspect, the articulation assembly may include an articulation actuation assembly operatively coupling the lever of the articulation lever assembly with the distal tube portion.

In another aspect, the articulation actuation assembly may include a translating rod and a linkage. The translating rod may be coupled to the lever of the articulation lever assembly such that pivoting of the lever imparts axial displacement of the translating rod. The linkage may pivotably couple the distal tube portion and the translating rod.

In yet another aspect, the linkage of the articulation actuation assembly may be configured to be received in the articulation joint when the distal tube portion is in a straight configuration.

In still yet another aspect, the slider may be biased away from the first pivot.

In still yet another aspect, the housing of the articulation lever assembly may be interposed between two halves of the camming support.

In still yet another aspect, the distal portion of the camming groove may include a first distal portion defining a first angle with respect to the transition portion, and a second distal portion defining a second angle with respect to the transition portion. The first distal portion may be interposed between the transition portion and the second distal portion. The first angle may be different from the second angle.

In an aspect, the second angle may be greater than the first angle.

In another aspect, the proximal portion of the camming groove may include a first proximal portion defining a third angle with respect to the transition portion, and a second proximal portion defining a fourth angle with respect to the transition portion. The first proximal portion may be interposed between the transition portion and the second proximal portion. The third angle may be different from the fourth angle.

In another aspect, the fourth angle may be greater than the third angle.

In yet another aspect, the first proximal portion may be substantially perpendicular to the transition portion.

In another aspect, the camming pin may be configured to rest in the second proximal and distal portions of the camming groove when the slider is in the respective proximal and distal positions.

BRIEF DESCRIPTION OF DRAWINGS

The above and other aspects and features of this disclosure will become more apparent in view of the following detailed description when taken in conjunction with the accompanying drawings wherein like reference numerals identify similar or identical elements.

FIG. 7 is an exploded perspective view of the endoscopic anchor retaining and advancing assembly;

FIG. 8 is a cross-sectional view the endoscopic surgical tack applier cut along section line 8-8 of FIG. 10;

FIG. 9 is an enlarged view of the indicated area of detail of FIG. 7, illustrating an articulation joint of the endoscopic anchor retaining and advancing assembly;

FIG. 9C is a cross-sectional view of the endoscopic anchor retaining and advancing assembly of FIG. 9A cut along section line 9C-9C of FIG. 9A;

FIG. 9D is a cross-sectional view of the endoscopic anchor retaining and advancing assembly of FIG. 9B cut along section line 9D-9D of FIG. 9B;

FIG. 10 is a partial cross-sectional view of the endoscopic surgical tack applier of FIG. 1;

FIG. 11 is an enlarged cross-sectional view of the indicated area of detail of FIG. 10;

FIG. 12 is a partial side view of the handle assembly of FIG. 1;

FIG. 13 is a partial side cross-sectional view of the endoscopic anchor retaining and advancing assembly;

FIG. 14 is a partial side view of the handle assembly of FIG. 12, illustrating a slider of the handle assembly in a proximal position to place a distal tube portion of the endoscopic anchor retaining and advancing assembly in an articulated configuration;

FIG. 15 is a partial side cross-sectional view of the endoscopic anchor retaining and advancing assembly, illustrating the distal tube portion in the articulated configuration.

DETAILED DESCRIPTION

Figure 1:
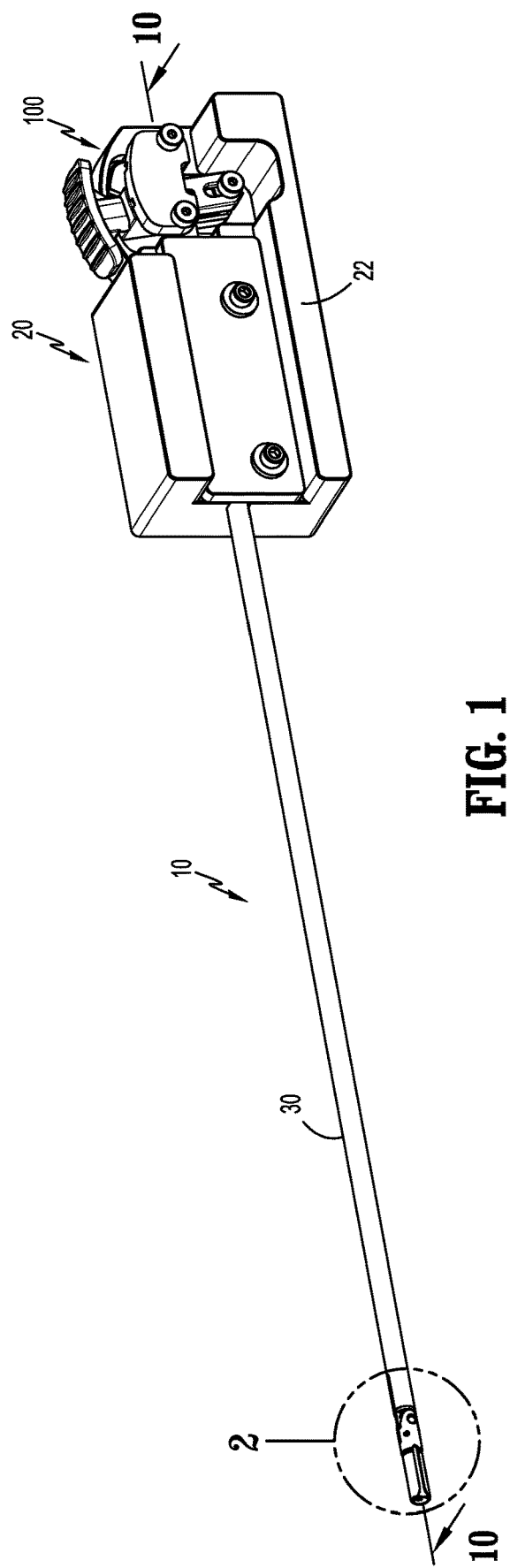
FIG. 1 is a perspective view of an endoscopic surgical tack applier in accordance with this disclosure.

The endoscopic surgical device disclosed herein is described in detail with reference to the drawings, in which like reference numerals designate identical or corresponding elements in each of the several views.

As used herein, the term "distal" refers to the portion that is being described which is further from a user, while the term "proximal" refers to the portion that is being described which is closer to a user. In addition, the terms parallel and perpendicular are understood to include relative configurations that are substantially parallel and substantially perpendicular up to about + or −10 degrees from true parallel and true perpendicular. Further, to the extent consistent, any or all of the aspects detailed herein may be used in conjunction with any or all of the other aspects detailed herein.

Accordingly, a need exists for an articulation mechanism configured for reduced backlash.

Non-limiting examples of endoscopic surgical devices which may include articulation joints according to the disclosure include manual, mechanical and/or electromechanical surgical tack appliers, surgical clip appliers, surgical staplers, surgical stitching devices and the like.

Figure 2:
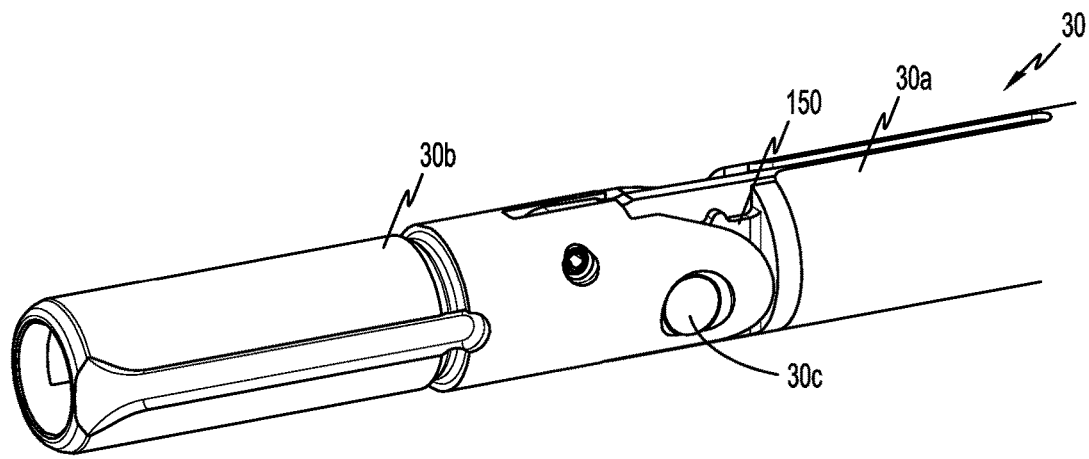
FIG. 2 is a partial perspective view of an endoscopic anchor retaining and advancing assembly of the endoscopic surgical tack applier of FIG. 1.
Figure 3:
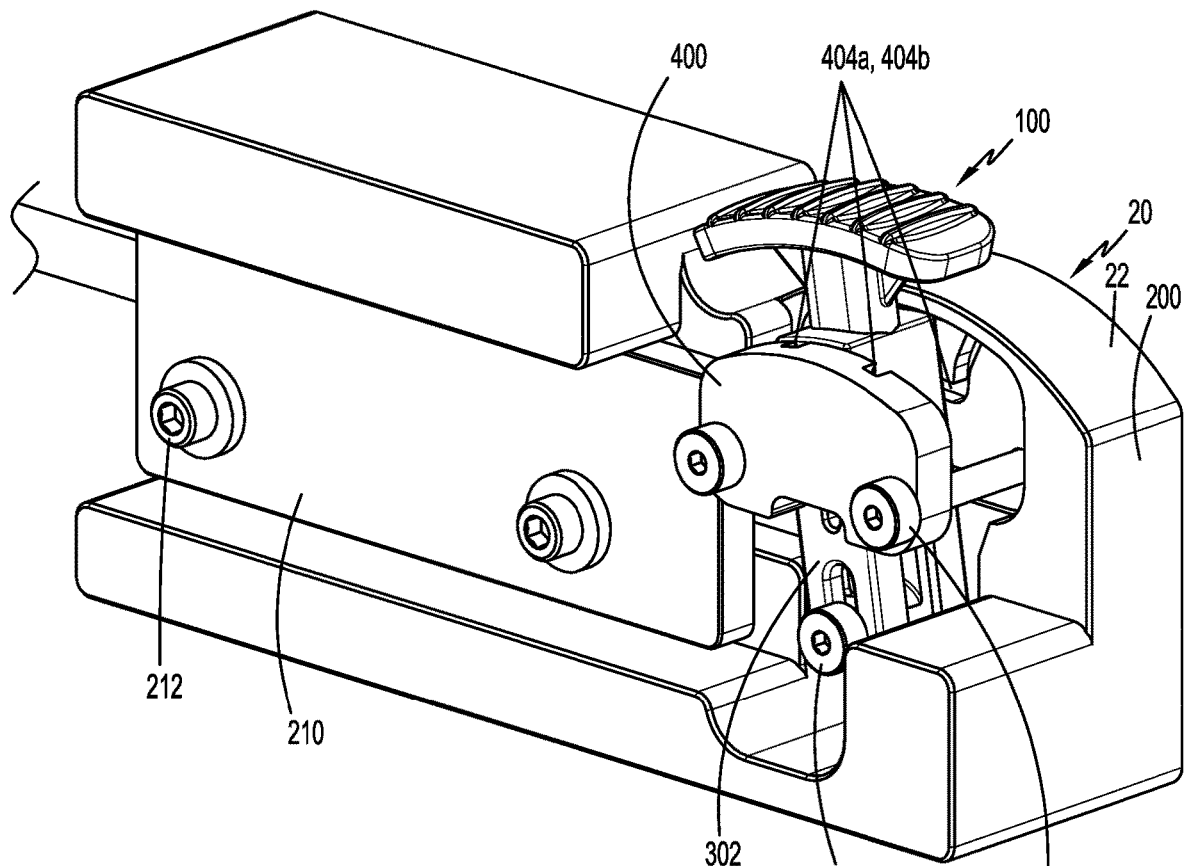
FIG. 3 is a handle assembly of the endoscopic surgical tack applier of FIG. 1.

In FIGS. 1-3, an exemplary articulation assembly for use with endoscopic surgical device, in the form of an endoscopic surgical tack applier 10 is shown generally as 100. The endoscopic surgical tack applier 10 includes a handle assembly 20, and an endoscopic anchor retaining/advancing assembly 30 extending from the handle assembly 20 and configured to store and selectively release or fire a plurality of anchors (not shown) therefrom. The endoscopic anchor retaining/advancing assembly 30 includes an articulation joint 150 provided along a length thereof. The endoscopic anchor retaining/advancing assembly 30 includes a proximal tube portion 30a, the articulation joint 150 supported on the proximal tube portion 30a, and a distal tube portion 30b pivotally connected to the articulation joint 150 by a pivot pin 30c. The articulation assembly 100 is configured for two-position actuation with backlash compensation. It is contemplated that while the articulation assembly 100 is configured for use with the endoscopic surgical tack applier 10, the articulation assembly 100 may be configured for use with other surgical instruments such as, e.g., surgical staplers or tissue graspers.

The handle assembly 20 includes a handle housing 22 including a button or a trigger (not shown) configured to fire the plurality of anchors from the endoscopic anchor retaining/advancing assembly 30. In particular, the trigger is operatively connected to a drive mechanism (not shown) such that each squeeze or actuation of the trigger results in a rotation of an inner shaft assembly (not shown) of the proximal tube portion 30a of anchor retaining/advancing assembly 30 which, in turn, fires the anchors. The drive mechanism may be mechanically actuated or may include an electro-mechanical configuration including a motor to actuate firing of the anchors.

Figure 4:
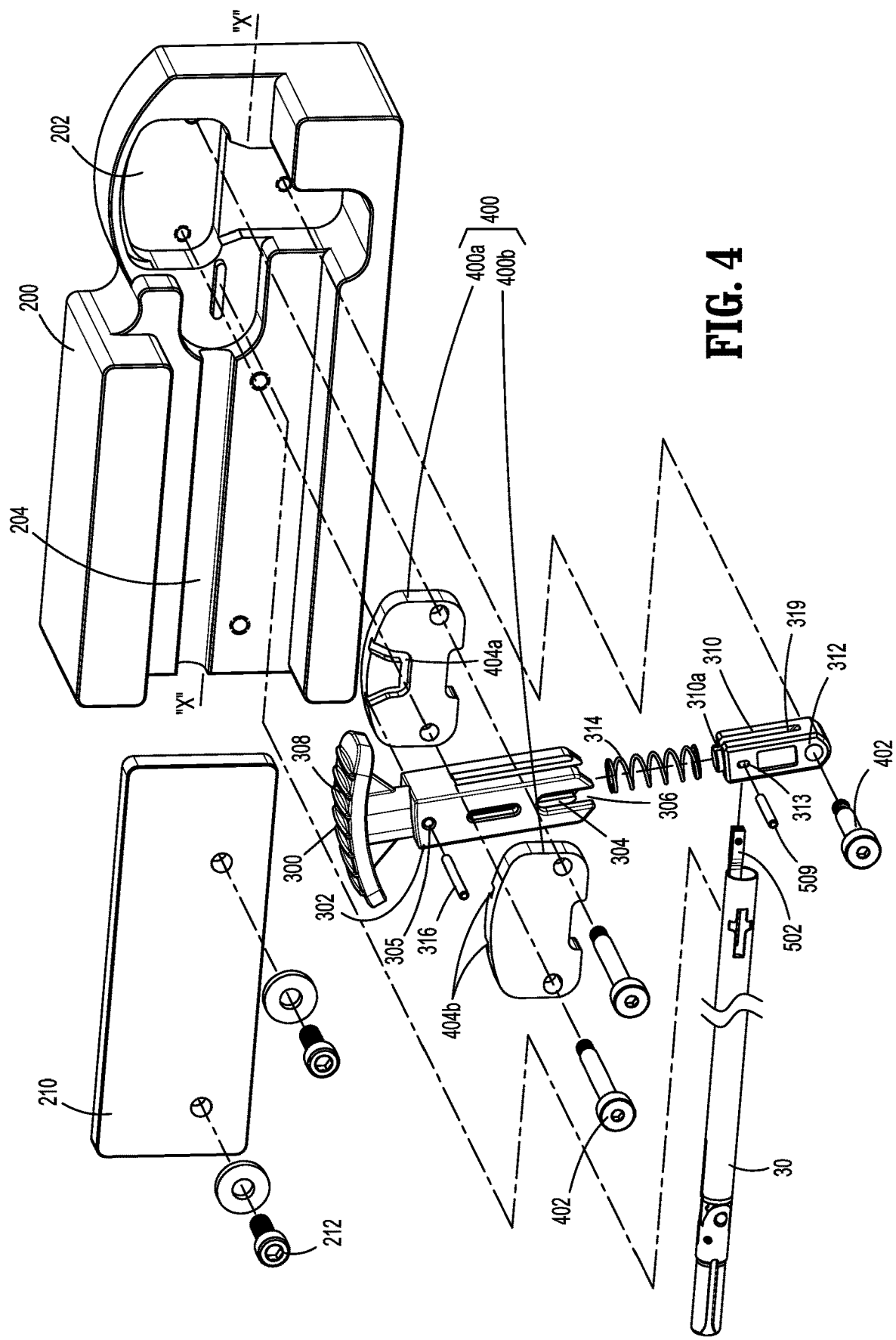
FIG. 4 is a partially exploded perspective view of the endoscopic surgical tack applier of FIG. 1, illustrating an articulation lever assembly.

FIGS. 3 and 4 illustrate the handle assembly 20 including the articulation assembly 100 in accordance with the disclosure. The articulation assembly 100 includes a body portion 200, an articulation lever assembly 300 operatively coupled with the distal tube portion 30b (FIG. 2) of the endoscopic anchor retaining/advancing assembly 30, and a camming support 400 configured to support the articulation lever assembly 300 therein. In particular, the body portion 200 defines a cavity 202 to securely receive a portion of the camming support 400 therein, and a groove 204 configured to receive the endoscopic anchor retaining/advancing assembly 30 therethrough. The body portion 200 may further include a panel 210 to secure a portion of the endoscopic anchor retaining/advancing assembly 30 in the groove 204. The panel 210 may include a flat surface configured to be in registration with the groove 204. For example, the panel 210 may be secured to the body portion 200 by screws 212.

The articulation lever assembly 300 includes a housing 302 defining a cavity 304 and an opening 306 in communication with the cavity 304, a slider 308 extending from the housing 302, and a lever 310 pivotably coupled to the body portion 200 about a pivot 312 by a screw 402. In particular, the lever 310 supports a biasing member 314 on an end portion 310a opposite of the pivot 312. The lever 310 and the biasing member 314 are configured to be received in the cavity 304 of the housing 302 through the opening 306. In addition, the biasing member 314 is secured to the lever 310 and the housing 302. The housing 302 and the slider 308 of the articulation lever assembly 300 may be formed as a single construct to enable movement as a single body. Under such a configuration, the housing 302 and the slider 308 are biased away from the pivot 312. The lever 310 defines a bore 313 configured to receive a pin 509 which couples translating rods 502 of an articulation actuation assembly 500 to the lever 310, as will be discussed below.

As shown in FIGS. 3 and 4, the camming support 400 includes first and second portions 400a, 400b. In particular, the first and second portions 400a, 400b define respective camming grooves 404a, 404b that are mirror images of each other. It is contemplated that the camming groove 404a, 404b may be defined in only one of the first and second portions 400a, 400b. The housing 302 is supported between the first and second portions 400a, 400b of the camming support 400. In particular, the housing 302 defines a lateral bore 305 extending therethrough such that a camming pin 316 extending through the lateral bore 305 cammingly engages the respective camming grooves 404a, 404b of the camming support 400. The first portion 400a of the camming support 400 is received in the cavity 202 of the body portion 200. Screws 402 may be used to secure the camming support 400 to the body portion 200.

Figure 5:
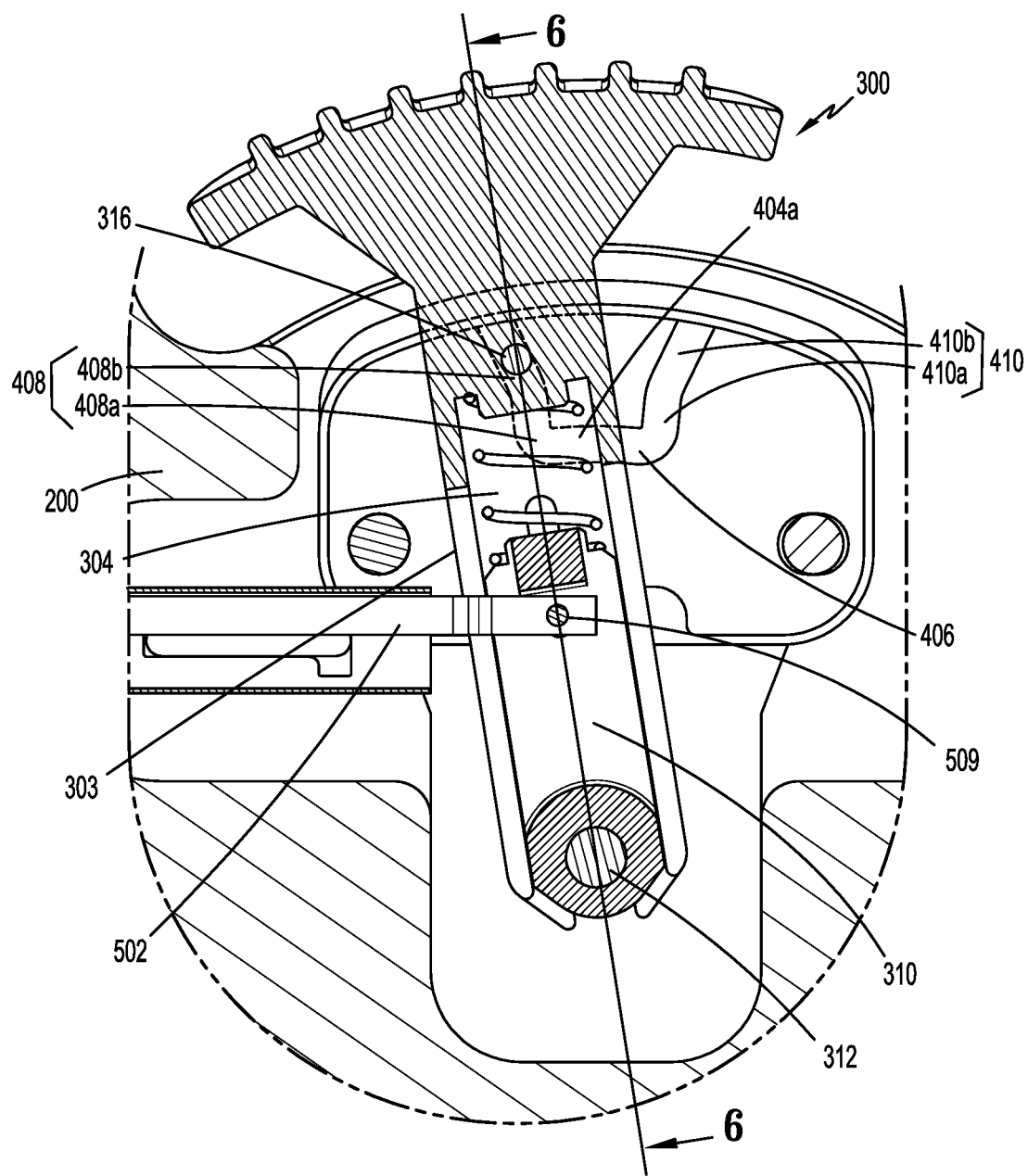
FIG. 5 is an enlarged cross-sectional view of the indicated area of detail of FIG. 10, illustrating the articulation lever assembly.
Figure 6:
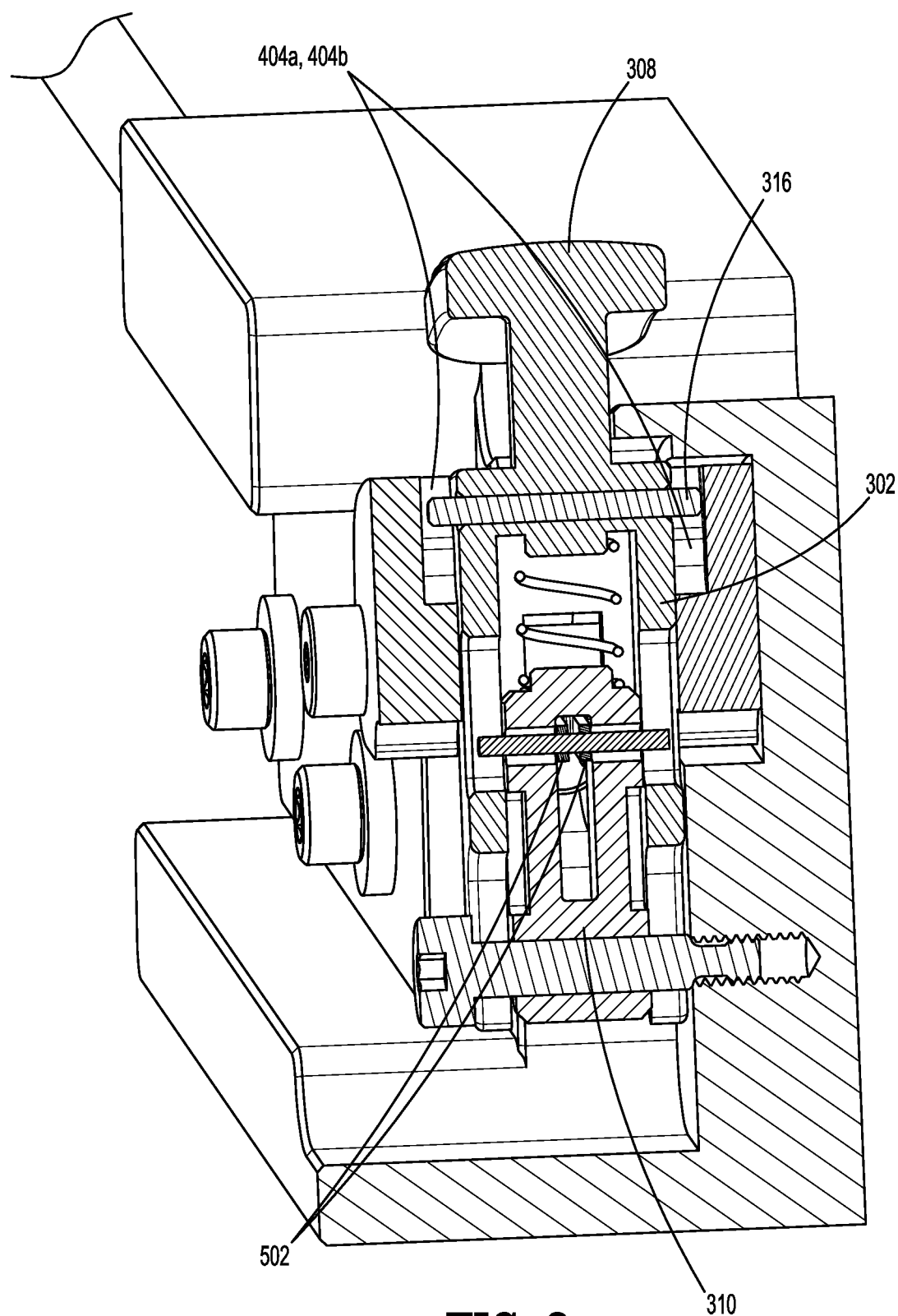
FIG. 6 is a cross-sectional view of the handle assembly cut along section line 6-6 of FIG. 5.

FIGS. 5 and 6 illustrate the articulation lever assembly 300 operatively supported on the body portion 200. As discussed hereinabove, the camming pin 316 of the housing 302 cammingly engages the camming grooves 404a, 404b of the camming support 400. The camming grooves 404a, 404b are mirror images of each other. In particular, each of the camming grooves 404a, 404b (only 404a shown in FIG. 5) has a transition portion 406, a distal portion 408, and a proximal portion 410. In particular, the transition portion 406 may be substantially parallel to a longitudinal axis "X-X" (FIG. 4) defined by the body portion 200. The distal portion of the camming grooves 404a, 404b may include a first distal portion 408a defining a first angle with respect to the transition portion 406 and a second distal portion 408b defining a second angle with respect to the transition portion 406. The second angle may be greater than the first angle. The first distal portion 408a interconnects the transition portion 406 and the second distal portion 408b. Similarly, the proximal portion 410 includes a first proximal portion 410a defining a third angle with respect to the transition portion 406 and a second distal portion 410b defining a fourth angle with respect to the transition portion 406. The fourth angle may be greater than the third angle. The first proximal portion 410a interconnects the transition portion 406 and the second proximal portion 410b. The first and third angles may be identical, and the second the fourth angles may be identical. For example, the first proximal and distal portions 408a, 410a may be substantially perpendicular to the transition portion 406. Under such a configuration, the camming pin 316 may rest in the second proximal and distal portions 408b, 410b of the respective proximal and distal portions 408, 410 of the camming grooves 404a, 404b when the slider 308 is in the respective proximal and distal positions. Under such a configuration, a clinician may depress the slider 308 prior to transitioning the slider 308 between the proximal and distal positions via the transition portion 406 such that the camming pin 316 is in registration with the transition portion 406. Such a configuration may remove any backlash associated with the articulation assembly 100.

Figure 6A:
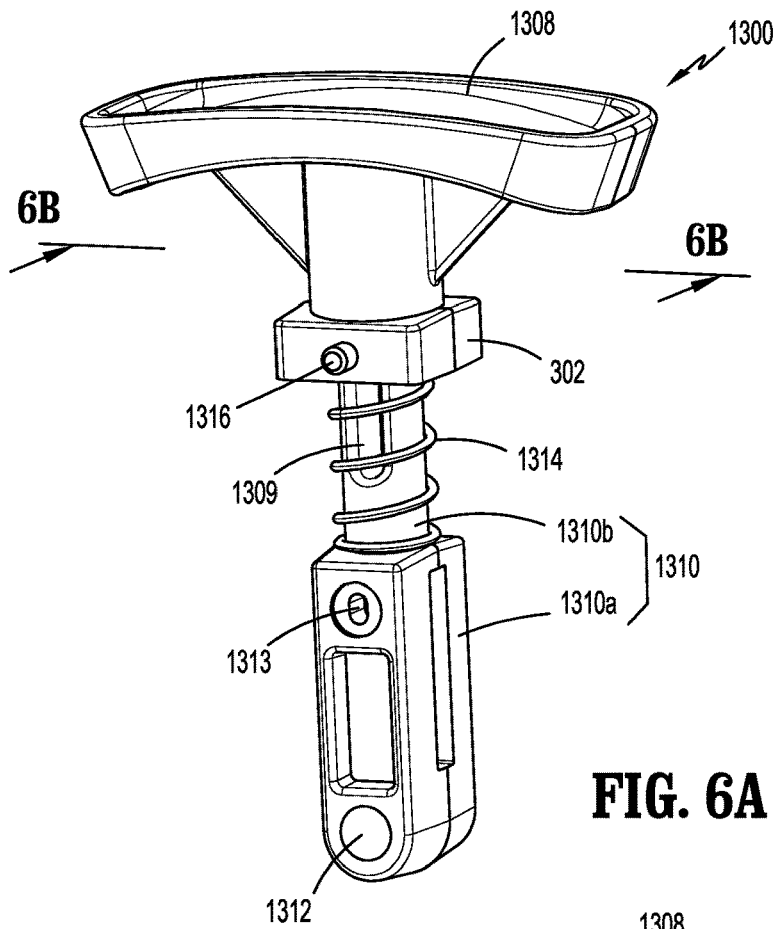
FIG. 6A is a perspective view of an articulation lever assembly for use with the articulation assembly of FIG. 4.
Figure 6B:
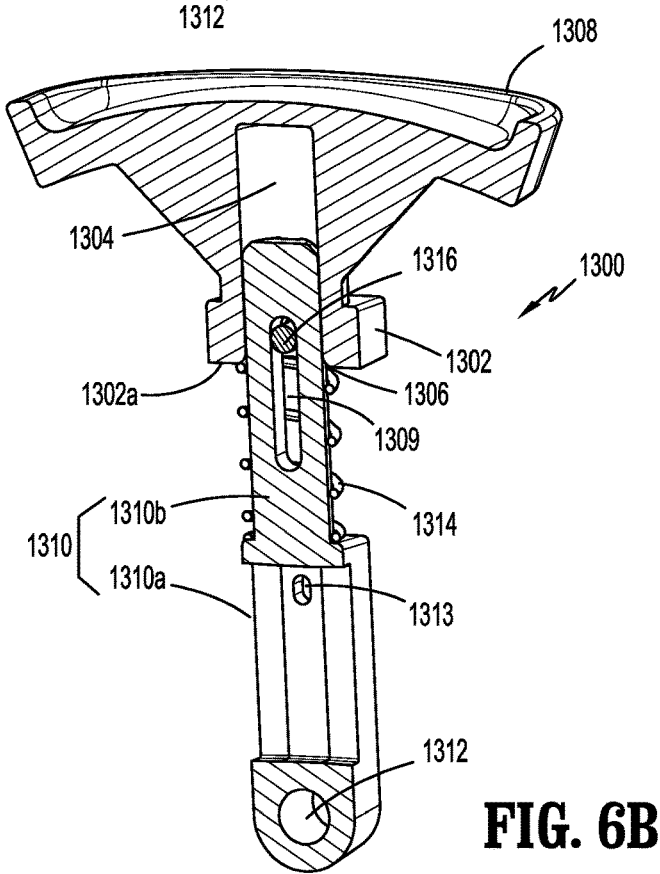
FIG. 6B is a cross-sectional view of the articulation lever assembly of FIG. 6A cut along section line 6B-6B of FIG. 6A.

FIGS. 6A and 6B illustrate an articulation lever assembly 1300 for use with the articulation assembly 100 (FIG. 1).

The articulation lever assembly 1300 includes a housing 1302 defining a cavity 1304 and an opening 1306 in communication with the cavity 304, a slider 1308 extending from the housing 1302, and a lever 1310 pivotably coupled to the body portion 200 (FIG. 4). The lever 1310 includes a base portion 1310a pivotably coupled to the body portion 200 about a pivot 1312 by a screw 402 (FIG. 4), and a stem portion 1310b extending from the base portion 1310a and slidably received in the cavity 1304 of the housing 1302. The stem portion 1310b supports a biasing member 1314 thereabout. While the stem portion 1310b is configured to be received in the cavity 1304 through the opening 1306 of the housing 1302, the biasing member 1314 is secured to an engaging surface 1302a of the housing 1302 and the base portion 1310a such that the housing 1302 is biased away from the base portion 1310a of the lever 1310. In particular, the stem portion 1310b defines a slot 1309 along a length thereof to receive a camming pin 1316 extending through the housing 1302. Under such a configuration, the housing 1302 and the slider 1308 are biased away from the pivot 1312. The lever 1310 defines a bore 1313 configured to receive the pin 509 (FIG. 4) which couples translating rods 502 (FIG. 4) of the articulation actuation assembly 500 to the lever 1310.

The housing 1302 may be supported between the first and second portions 400a, 400b (FIG. 4) of the camming support 400. In particular, the housing 1302 defines a lateral bore (not shown) extending therethrough such that the camming pin 1316 extending through the lateral bore cammingly engages the respective camming grooves 404a, 404b of the camming support 400. In contrast to the articulation lever assembly 300, when the slider 1308 is depressed, the housing 1302 does not extend beyond the pivot 1312, which, in turn, enables the housing 1302 to be closer to the pivot 1312.

FIGS. 6 and 7 further illustrate the articulation assembly 100 further including an articulation actuation assembly 500 operatively coupled with the lever 310 such that pivoting of the lever 310 (FIG. 5) between the proximal and distal positions transitions the distal tube portion 30b between the straight and articulated configurations. The articulation actuation assembly 500 includes a pair of translating rods 502 coupled with the lever 310 of the articulation lever assembly 300. In particular, the pair of translating rods 502 is coupled with the lever 310 by a pin 509. The housing 302 defines a window 303 (FIG. 5) configured to receive the pair of translating rods 502 therethrough. The translating rods 502 are slidably supported in a channel 511 defined in an inner support member 508 as shown in FIG. 7. The inner support member 508 is disposed within an outer tube 33 of the endoscopic anchor retaining/advancing assembly 30. The inner support member 508 may further define a longitudinal passage 519 configured to receive a drive member (not shown) to apply the tacks, as known by one skilled in the art.

As shown in FIG. 7, the translating rods 502 are coupled to a linkage 507 by a pin 505. In particular, a proximal end portion 507a of the linkage 507 is coupled with respective distal end portions 503 of the translating rods 502 by the pin 505, and a distal end portion 507b of the linkage 507 is coupled with the distal tube portion 30b. The distal tube portion 30b defines a bore 37 configured to receive a pin 35 to be pivotably coupled with a distal end portion 507b of the linkage 507 of the articulation actuation assembly 500. The endoscopic anchor retaining/advancing assembly 30 further includes the articulation joint 150 (FIG. 9) coupled to a distal end portion 33b of the outer tube 33.

FIG. 9 illustrates the articulation joint 150 including opposing lateral walls 154 defining a cavity 151 therebetween. The articulation joint 150 includes opposing portions having a closed portion 157 and an opening 155 between the opposing lateral walls 154. The linkage 507 is configured to be received in the cavity 151 through the opening 155. The opposing lateral walls 154 define respective lateral bores 152 configured to receive respective pins 515 to be pivotably coupled with the distal tube portion 30b. Under such a configuration, axial displacement of the translating rods 502 causes articulation of the distal tube portion 30b about the pins 515. The opposing lateral walls 154 include respective distal surfaces 160. The distal surfaces 160 extend between the opening 155 and the closed portion 157. The distal surfaces 160 may define an arcuate profile or a curvature. Each distal surface 160 includes a protrusion 162 configured to engage the distal tube portion 30b in a straight configuration in which the distal tube portion 30b is axially aligned with the proximal tube portion 30a. The protrusion 162 is formed of, e.g., deformable or resilient material, to enhance engagement with the distal tube portion 30b to limit articulation of the distal tube portion 30b. The protrusion 162 is configured to provide rigid engagement of the distal tube protrusion 30b with the articulation joint 150, e.g., during and/or after, transition to the straight configuration.

The opposing lateral walls 154 further include respective engagement surfaces 170. The engagement surfaces 170 are disposed adjacent the opening 155. The engagement surface 170 may be substantially parallel to a longitudinal axis "L-L" defined by the articulation joint 150. The engagement surfaces 170 include respective protrusions 172 configured to engage the distal tube portion 30b to limit articulation of the distal tube portion 30b, e.g., during and/or after, transition of the distal tube portion 30b to an articulated configuration in which the distal tube portion 30b is axially offset from the proximal end portion 33a. The protrusions 172 may be formed of, e.g., deformable or resilient material, to enhance engagement with the distal tube portion 30b. The protrusion 172 is configured to provide rigid engagement of the distal tube portion 30b with the articulation joint 150, e.g., during and/or after, transition of the distal tube portion 30b to the articulated configuration.

Figure 9A:
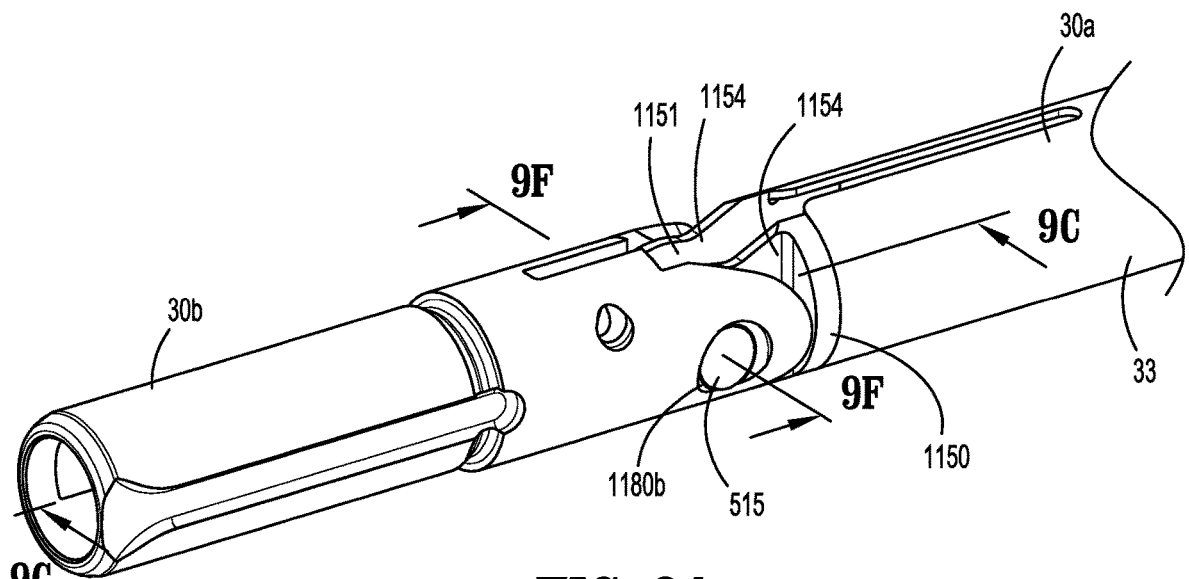
FIGS. 9A and 9B are partial perspective views of an endoscopic anchor retaining and advancing assembly for use with the endoscopic surgical tack applier of FIG. 1 in accordance with the disclosure.
Figure 9B:
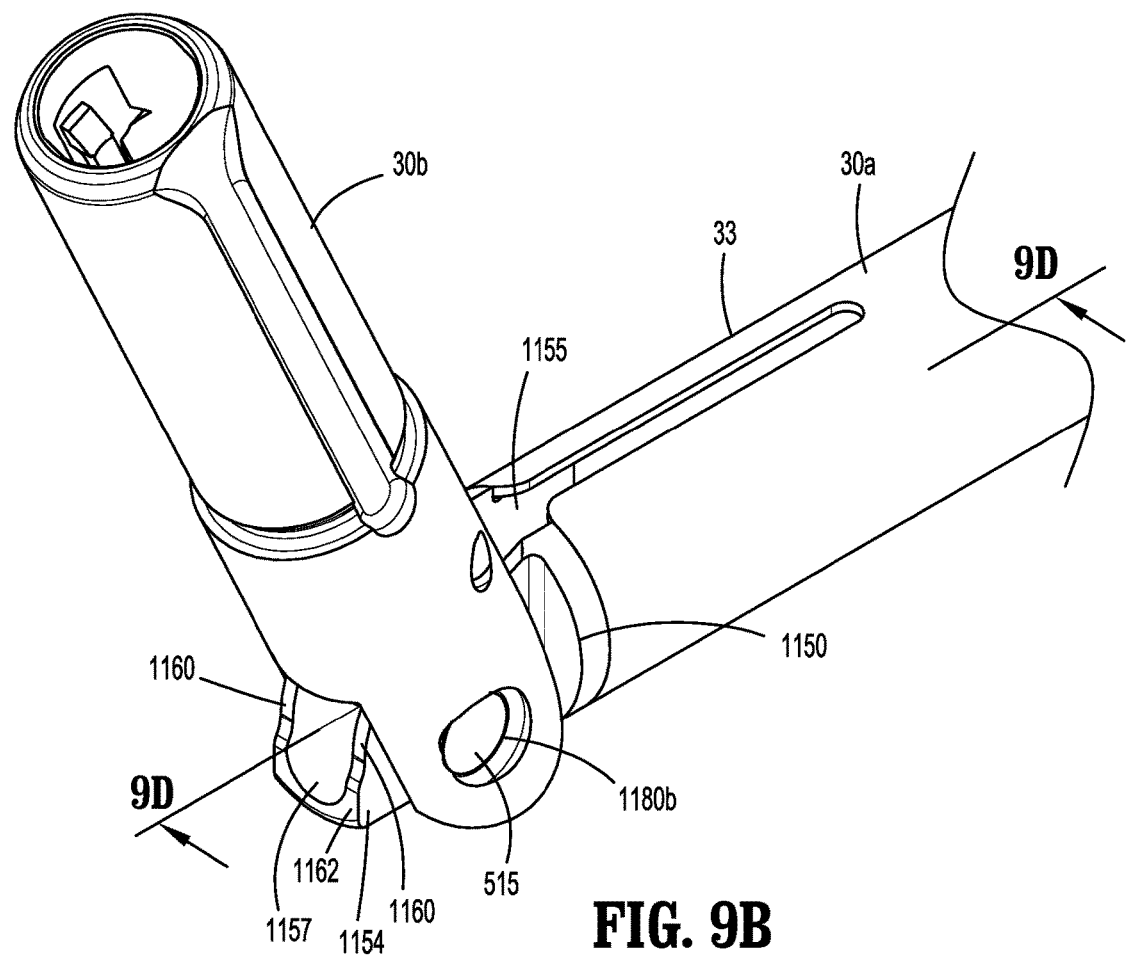

FIGS. 9A and 9B show an articulation joint 1150 for use with the endoscopic anchor retaining/advancing assembly 30 (FIG. 4) in accordance with the disclosure. The articulation joint 1150 is supported on the proximal tube portion 30a. In contrast to the articulation joint 150 (FIG. 9) including the protrusions 162, 192 that serve as stops for the distal tube portion 30b, the articulation joint 1150 includes opposing lateral walls 1154 that have contours or planar surfaces that serve as stops for the distal tube portion 30b.

The articulation joint 1150 includes opposing lateral walls 1154 defining a cavity 1151 therebetween. The articulation joint 1150 includes opposing portions having a closed portion 1157 and an opening 1155 between the opposing lateral walls 1154. The linkage 507 (FIG. 7) is configured to be received in the cavity 1151 through the opening 1155. The opposing lateral walls 1154 define respective lateral bores 1154b (FIG. 9E) configured to receive respective pins 515. Under such a configuration, axial displacement of the translating rods 502 causes articulation of the distal tube portion 30b about the pins 515. The opposing lateral walls 1154 include respective distal surfaces 1160. The distal surfaces 1160 extend between the opening 1155 and the closed portion 1157. Each distal surface 1160 includes a distal stop 1162 configured to engage the distal tube portion 30b in a straight configuration in which the distal tube portion 30b is axially aligned with the proximal tube portion 30a. In particular, the distal stop 1162 defines a plane substantially orthogonal to a longitudinal axis "Y-Y" defined by the articulation joint 1150. The distal stop 1162 may be formed of, e.g., deformable or resilient material, to enhance engagement with the distal tube portion 30b. The distal stop 1162 is configured to provide rigid engagement of the distal tube protrusion 30b with the articulation joint 150 to provide a stop and a frictional securement of the distal tube portion 30b with the distal stop 1162.

The opposing lateral walls 1154 further include respective engagement surfaces 1170. The engagement surfaces 1170 are disposed adjacent the opening 1155. The engagement surfaces 1170 include respective proximal stops 1172 configured to engage the distal tube portion 30b to frictionally secure the distal tube portion 30b to the articulated configuration in which the distal tube portion 30b is axially offset from the proximal tube portion 30a. The proximal stop 1172 may be formed of, e.g., deformable or resilient material, to enhance engagement with the distal tube portion 30b. In particular, the proximal stop 1172 defines a plane forming an acute angle with respect to the longitudinal axis "Y-Y" of the articulation joint 1150. The proximal stop 1172 is configured to provide rigid engagement of the distal tube protrusion 30b with the articulation joint 150, e.g., during and/or after, transition of the distal tube portion 30b to the articulated configuration.

FIGS. 9C and 9D illustrate the distal and proximal stops 1162, 1172 of the articulation joint 1150 engaging the respective first and second proximal faces 37a, 37b of the distal tube portion 30b. As discussed above, the distal surface 1160 includes the distal stop 1162 that is substantially orthogonal to the longitudinal axis "Y-Y," and the engagement surface 1170 includes the proximal stop 1172 that defines an acute angle with respect to the longitudinal axis "Y-Y." Under such a configuration, the distal stop 1162 and the first proximal face 37a are in a planar contact when the distal tube portion 30b is in the straight configuration, in which, the distal tube portion 30b is axially aligned with the proximal tube portion 30a, and the proximal stop 1172 and the second proximal face 37b are in planar contact when the distal tube portion 30a is in the articulated configuration. In addition, the distal surface 1160 and the engagement surface 1170 include an arcuate portion that connects the distal and proximal stops 1162, 1172.

Figure 16:
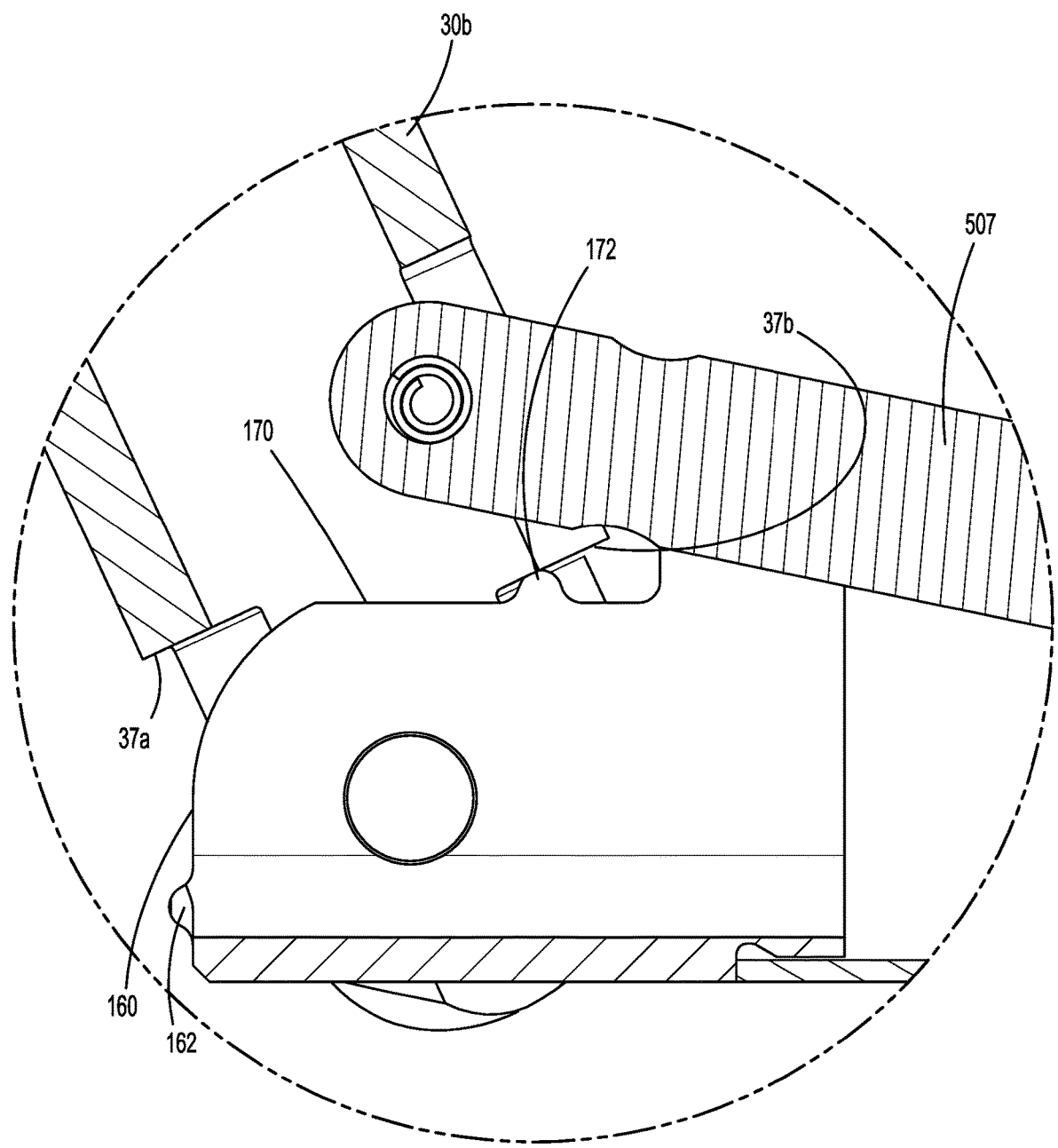
FIG. 16 is an enlarged cross-sectional view of the indicated area of detail of FIG. 15.

FIGS. 10 and 11 illustrate the articulation assembly 100 in the straight configuration in which the distal tube portion 30b is axially aligned with the proximal tube portion 30a. In particular, the slider 308 of the articulation lever assembly 300 is in a distal position in which the camming pin 316 rests in the second distal portion 408b of the camming grooves 404a, 404b. At this time, the protrusions 162 (FIG. 9) of the respective distal faces 160 of the articulation joint 150 engage a first proximal face 37a (FIG. 16) of the distal tube portion 30b. Under such a configuration articulation of the distal tube portion 30b may be limited by the protrusions 162. The distal tube portion 30b may be transitioned to the articulated configuration, in which, the distal tube portion 30b is axially offset from the proximal tube portion 30a (FIG. 15). In particular, the slider 308 of the articulation lever assembly 300 is depressed in the direction of an arrow "D" (FIG. 12) such that the camming pin 316 slides to be in registration with the transition portion 406 of the camming grooves 404a, 404b. The slider 308 may be displaced proximally in the direction of arrow "P" to displace the camming pin 316 to the proximal-most portion of the transition portion 406. At this time, the slider 308 may be released such that the camming pin 316 is urged towards the second proximal portion 410b in the direction of an arrow "U" (FIG. 14) via the first proximal portion 410a. As the camming pin 316 is displaced to the proximal portion 410 of the camming grooves 404a, 404b, the lever 310 pivots about the pivot 312, which, in turn, retracts the translating rods 502 proximally (FIG. 13). Retraction of the translating rods 502 causes the linkage 507 to transition the distal tube portion 30b to the articulated configuration (FIG. 15), during which, a second proximal face 37b (FIG. 16) of the distal tube portion 30b engages the protrusions 172 of the engagement surfaces 170 of the articulation joint 150. Under such a configuration, the protrusions 172 serve as a stop during and/or after transition of the distal tube portion 30b towards the articulated configuration.

Figure 9E:
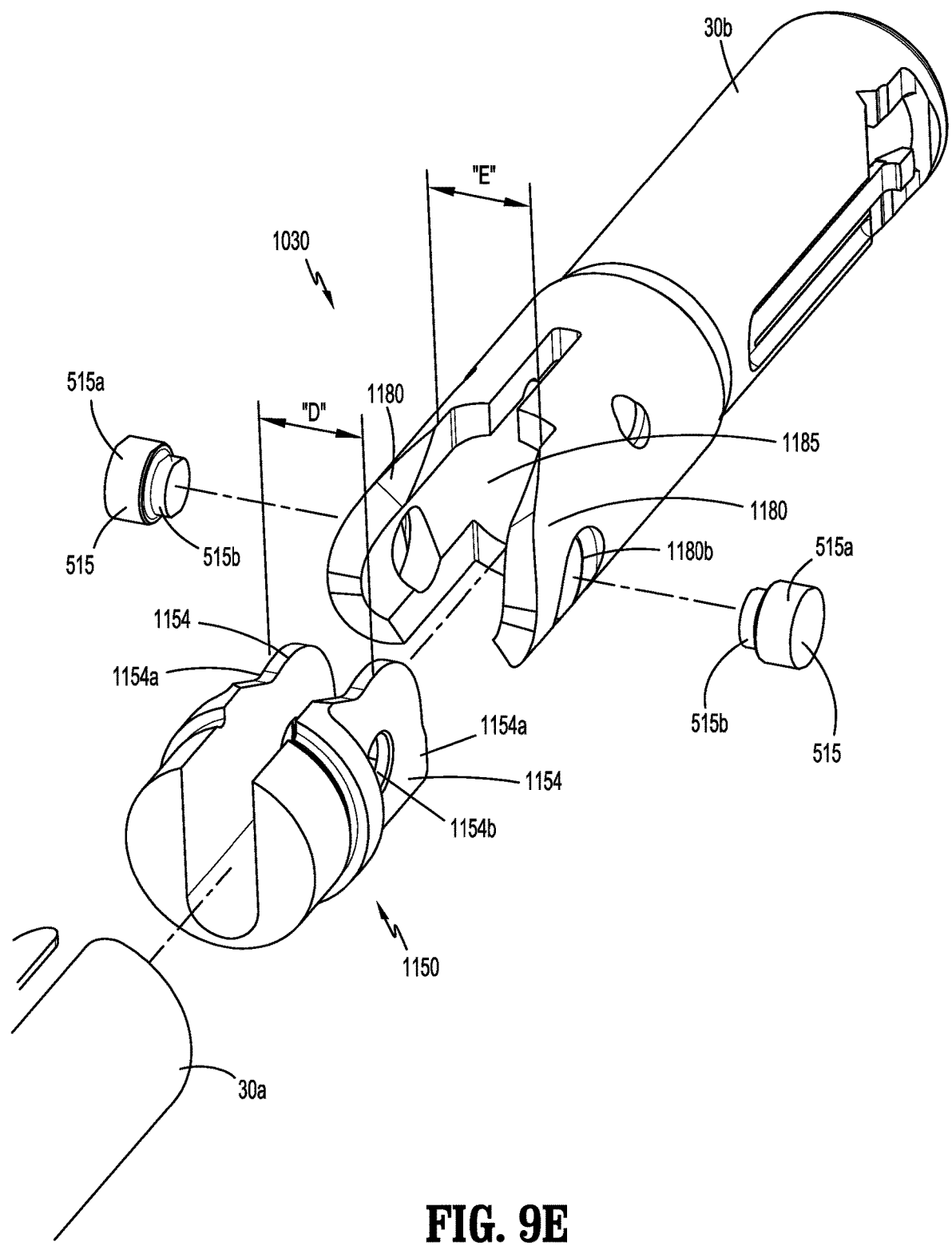
FIG. 9E is a partial perspective view of the endoscopic anchor retaining and advancing assembly of FIG. 9A with parts separated.
Figure 9F:
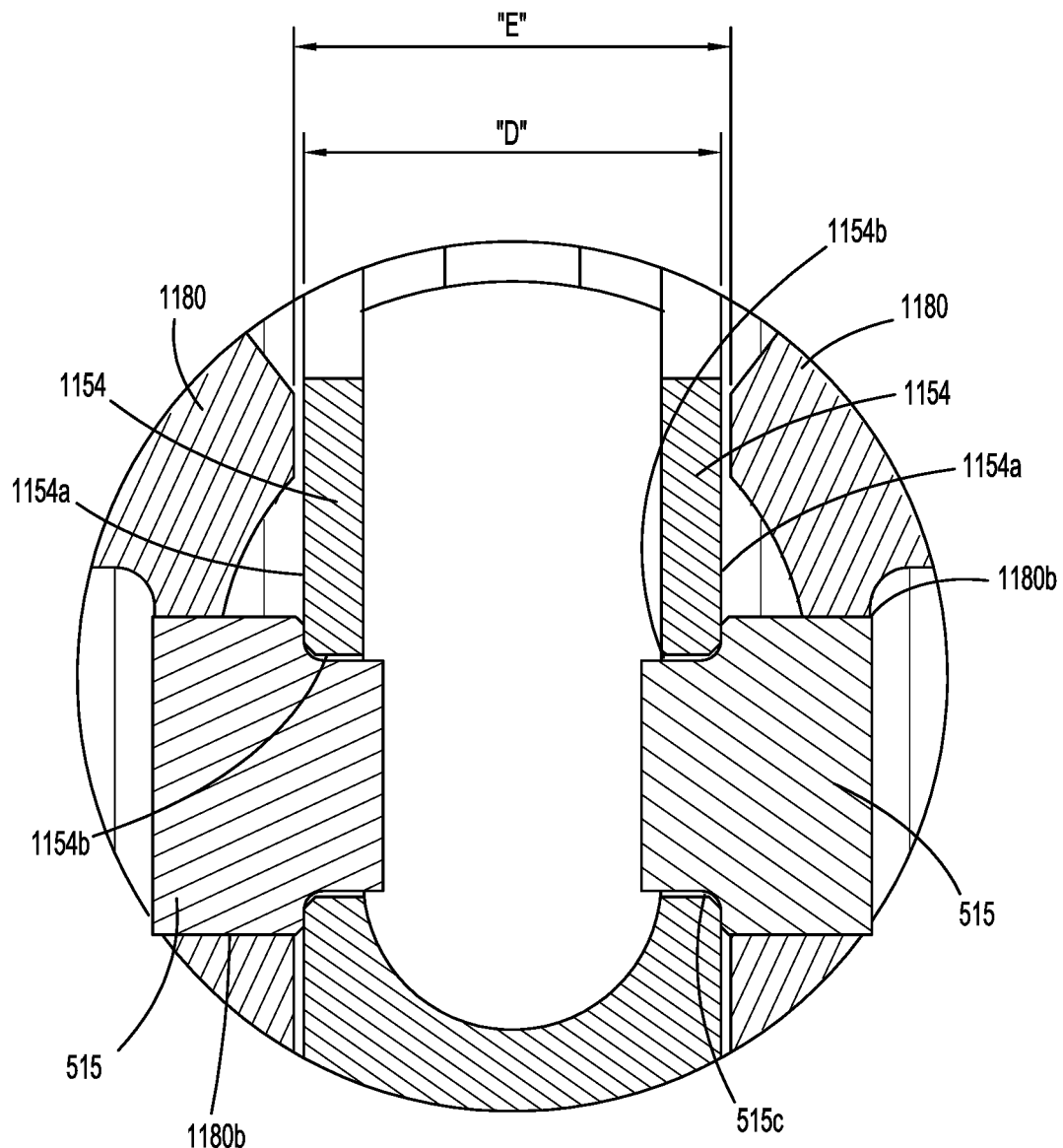
FIG. 9F is a cross-sectional view of the endoscopic anchor retaining and advancing assembly of FIG. 9A cut along section line 9F-9F of FIG. 9A.

While the articulation assembly 100 has been shown to reduce axial backlash, FIGS. 9E and 9F show the endoscopic anchor retaining/advancing assembly 1030 including the articulation joint 1150 configured to reduce lateral backlash. While the endoscopic anchor retaining/advancing assembly 1030 is shown to reduce lateral backlash, it is also contemplated that the endoscopic anchor retaining/advancing assembly 30 may also be configured to reduce lateral backlash. As discussed hereinabove, the articulation joint 1150 is supported on the proximal tube portion 30a. The lateral walls 1154 of the articulation joint 1150 include respective outer surfaces 1154a defining a distance "D" therebetween. The distal tube portion 30b includes a pair of lateral wings 1180 defining a mouth 1185 dimensioned to receive the lateral walls 1154 of the articulation joint 1150 therein. In particular, the mouth 1185 has a width "E" larger than the distance "D". In particular, the lateral walls 1154 define respective bores 1154b dimensioned to receive a neck portion 515b of the pin 515. The lateral wings 1180 define respective bores 1180b configured to receive a head portion 515a of the pin 515. The pin 515 further includes a shoulder 515c interconnecting the head portion 515a and the neck portion 515. The shoulder 515c is configured to engage the lateral wall 1154 of the articulation joint 1150. For example, the shoulder 515c of the pin 515 and the lateral wall 1154 may be rounded or beveled to facilitate pivotable engagement therebetween. Further, the head portion 515a of the pin 515 is fixed to the lateral wing 1180 of the distal tube portion 30b by, e.g., welding, brazing, soldering, press fitting, spin welding, gluing, etc. Under such a configuration, the pins 515 are spaced apart. In this manner, a pair of opposing pins 515 laterally secures the articulation joint 1150 supported on the proximal tube portion 30a, thereby reducing lateral backlash.

In use, the articulation assembly 100 is initially placed in the straight configuration in which the slider 308 is positioned in the distal position such that the camming pin 316 is placed in the distal portion 408 of the camming groove 404a, 404b. At this time, the clinician may position the distal tube portion 30b adjacent a target tissue. Thereafter, the slider 308 may be transitioned to the proximal position to transition the distal tube portion 30b to the articulation configuration. The endoscopic surgical tack applier 10 may be actuated to apply tacks to tissue and/or mesh (not shown) as needed.

It is contemplated that tack applier 100 may be configured such that distal tube portion 130b of anchor retaining/advancing assembly 30 is configured and adapted to releasably and selectively receive a disposable loading unit (DLU) or single use loading unit (SULU), wherein the DLU or SULU includes at least an outer tube, a coil or helical thread provided along an interior of the outer tube, and an inner shaft rotatably disposed within the coil or helical thread. The inner shaft may include a splined distal end portion configured to support at least one anchor, and a proximal end portion configured and adapted for mechanical and non-rotational connection to a distal end of an exemplary intermediate flexible drive cable (not shown). It is also envisioned that the articulation assembly 100 may be configured to connect to a robotic arm of a robotic surgical system to enable manipulation and control thereof.

While the disclosure has been shown in the drawings, it is not intended that the disclosure be limited thereto, as it is intended that the disclosure be as broad in scope as the art will allow and that the specification be read likewise. Therefore, the above description should not be construed as limiting, but merely as exemplifications. Those skilled in the art will envision other modifications within the scope and spirit of the claims appended hereto.

What is claimed is:

1. An articulation assembly for use with a surgical instrument comprising:
    a first portion;
    an articulation joint coupled to the first portion;
    a second portion pivotably coupled to the articulation joint such that the second portion is transitionable between a surgical instrument straight configuration in which the second portion is axially aligned with the first portion, and a surgical instrument articulated configuration in which the second portion is axially offset from the first portion; and
    an articulation assembly including:
        a body portion;
        an articulation lever assembly operatively coupled with the second portion, the articulation lever assembly including:
            a camming pin;
            a housing defining a cavity and lateral bores receiving the camming pin such that the camming pin extends laterally outward from the housing;
            a slider extending from the housing; and
            a lever pivotably coupled to the body portion about a first pivot, the lever at least partially received in the cavity of the housing;
        a camming support defining a camming groove cammingly engaging the camming pin, the camming groove including a transition portion, a distal portion, and a proximal portion, the transition portion interposed between the distal portion and the proximal portion, the distal portion and the proximal portion defining respective angles with respect to the transition portion, wherein:
            the distal portion of the camming groove includes:
                a first distal portion defining a first angle with respect to the transition portion, and
                a second distal portion defining a second angle with respect to the transition portion, the first distal portion interposed between the transition portion and the second distal portion, the first angle different from the second angle; and
            the proximal portion of the camming groove includes:
                a first proximal portion defining a third angle with respect to the transition portion, and
                a second proximal portion defining a fourth angle with respect to the transition portion, the first proximal portion interposed between the transition portion and the second proximal portion, the third angle different from the fourth angle;
    wherein the slider of the articulation lever assembly is transitionable between:
        a distal position, in which, the camming pin is in the distal portion of the camming groove and the second portion is in the surgical instrument straight configuration, and
        a proximal position, in which, the camming pin is in the proximal portion of the camming groove and the second portion is in the surgical instrument articulated configuration.

2. The articulation assembly according to claim 1, wherein the articulation assembly includes an articulation actuation assembly operatively coupling the lever of the articulation lever assembly with the second portion such that pivoting of the lever causes transition of the second portion between the surgical instrument straight and the surgical instrument articulated configurations.

3. The articulation assembly according to claim 2, wherein the articulation actuation assembly includes:
    a translating rod coupled to the lever of the articulation lever assembly such that pivoting of the lever imparts axial displacement to the translating rod; and
    a linkage pivotably coupling the second portion and the translating rod.

4. The articulation assembly according to claim 3, wherein the linkage of the articulation actuation assembly is receivable in the articulation joint when the second part is in the surgical instrument straight configuration.

5. The articulation assembly according to claim 1, wherein the lever of the articulation lever assembly includes a biasing member receivable in the cavity of the housing such that the slider is biased away from the first pivot.

6. The articulation assembly according to claim 1, wherein the transition portion of the camming groove is substantially parallel to a longitudinal axis defined by the body portion.

7. The articulation assembly according to claim 1, wherein the housing of the articulation lever assembly is interposed between two halves of the camming support.

8. The articulation assembly according to claim 1, wherein the housing and the slider of the articulation lever assembly are formed as a single construct.

9. The articulation assembly according to claim 1, wherein the camming pin rests in the second proximal portion and the second distal portion of the camming groove when the slider is in the respective proximal position and distal position.

10. An articulation system for use with a surgical instrument comprising:
    a first portion;
    an articulation joint coupled to the first portion, the articulation joint defining a cavity, the articulation joint including a distal surface including a first stop, and an engagement surface including a second stop;
    a second portion pivotably coupled to the articulation joint, the second portion transitionable between a surgical instrument straight configuration, in which, the second portion is axially aligned with the first portion and engages the first stop of the articulation joint, and a surgical instrument articulated configuration, in which, the second portion is axially offset from the first portion and engages the second stop of the articulation joint; and an articulation assembly including:
  a body portion;
  an articulation lever assembly operatively coupled with the second portion, the articulation lever assembly including:
    a housing defining a cavity;
    a camming pin extending laterally outward from the housing;
    a slider extending from the housing; and
    a lever pivotably coupled to the body portion and at least partially received in the cavity of the housing; and
  a camming support defining a camming groove cammingly engaging the camming pin, the camming groove including a transition portion, a distal portion, and a proximal portion, the transition portion interposed between the distal portion and the proximal portion, the distal portion and the proximal portion defining respective angles with respect to the transition portion,
  wherein the slider of the articulation lever assembly is transitionable between:
    a distal position, in which, the camming pin is in the distal portion of the camming groove such that the second portion is in the surgical instrument straight configuration, and
    a proximal position, in which, the camming pin is in the proximal portion of the camming groove such that the second portion is in the surgical instrument articulated configuration.

11. The articulation system according to claim 10, wherein the second portion includes a first proximal surface for engaging the first stop of the articulation joint when the second portion is in the surgical instrument straight configuration, and a second proximal surface for engaging the second stop of the articulation joint when the second portion is in the surgical instrument articulated configuration.

12. The articulation system according to claim 10, wherein the first stop or the second stop of the articulation joint is formed of deformable or resilient materials.

13. The articulation system according to claim 12, wherein the articulation joint includes opposing lateral walls defining the cavity between the opposing lateral walls, the articulation joint including opposing portions having a closed portion and an opening between the opposing lateral walls, the opposing lateral walls including respective distal surfaces extending between the closed portion and the opening, the distal surfaces including respective first stops, the opposing lateral walls including respective engagement surfaces disposed adjacent the opening, the engagement surfaces including respective second stops.

14. The articulation assembly according to claim 10, wherein the articulation assembly further includes an articulation actuation assembly operatively coupled with the lever such that pivoting of the lever between the proximal position and the distal position causes axial displacement of the articulation actuation assembly.

15. The articulation system according to claim 13, wherein the second portion includes opposing lateral wings defining a mouth dimensioned to receive the opposing lateral walls of the articulation joint, each lateral wing defining a bore and each lateral wall defining a hole in registration with the bore.

16. The articulation system according to claim 15, wherein the second portion is pivotably coupled to the articulation joint by a pair of pins, each pin having a head portion, a neck portion, and a shoulder connecting the neck portion to the head portion, the neck portion having a diameter smaller than a diameter of the head portion, the head portion fixedly received in the bore of the corresponding lateral wing and the neck portion extending through the hole of the corresponding lateral wall such that the shoulder engages the corresponding lateral wall.

17. The articulation system according to claim 16, wherein the shoulder of the pin is beveled or rounded.

18. The articulation system according to claim 10, wherein the lever of the articulation lever assembly includes a base portion pivotably coupled to the body portion about a pivot and a stem portion extending from the base portion and slidably received in the cavity of the housing, the stem portion supporting a biasing member about the stem portion, the biasing member secured with the housing and the base portion to bias the housing away from the pivot.

* * * * *